US010806812B2

(12) United States Patent
Barron et al.

(10) Patent No.: US 10,806,812 B2
(45) Date of Patent: Oct. 20, 2020

(54) MULTIPLE LIGHT EMITTER FOR INACTIVATING MICROORGANISMS

(71) Applicant: Vital Vio, Inc., Troy, NY (US)

(72) Inventors: Robert Barron, Port Washington, NY (US); Cori Winslow, Rensselaer, NY (US); Nicholas Jones, Mechanicville, NY (US)

(73) Assignee: Vital Vio, Inc., Troy, NY (US)

( * ) Notice: Subject to any disclaimer, the term of this patent is extended or adjusted under 35 U.S.C. 154(b) by 0 days.

(21) Appl. No.: 16/369,484

(22) Filed: Mar. 29, 2019

(65) Prior Publication Data

US 2019/0298870 A1 Oct. 3, 2019

Related U.S. Application Data

(63) Continuation of application No. 15/940,127, filed on Mar. 29, 2018, now Pat. No. 10,413,626.

(51) Int. Cl.
*A61L 2/10* (2006.01)
*H01L 25/075* (2006.01)
(Continued)

(52) U.S. Cl.
CPC ................. *A61L 2/10* (2013.01); *A61L 2/084* (2013.01); *A61L 2/085* (2013.01); *A61L 9/18* (2013.01); *A61N 5/0624* (2013.01); *H01L 25/0753* (2013.01); *H01L 33/502* (2013.01); *A61L 2202/11* (2013.01); *A61N 2005/0651* (2013.01); *A61N 2005/0661* (2013.01);
(Continued)

(58) Field of Classification Search
CPC ............. A61L 2/00; A61L 2/0047; A61L 2/10
USPC ........................................ 250/453.11, 455.11
See application file for complete search history.

(56) References Cited

U.S. PATENT DOCUMENTS 1,493,820 A 5/1924 Miller et al.
2,622,409 A 12/1952 Stimkorb
(Continued)

FOREIGN PATENT DOCUMENTS

CN 201396611 Y 2/2010
CN 102213382 A 10/2011
(Continued)

OTHER PUBLICATIONS

Burkhart, C. G. et al., "Acne: a review of immunologic and microbiologic factors," Postgraduate Medical Journal, 1999, vol. 75, pp. 328-331.
(Continued)

*Primary Examiner* — Jason L McCormack
(74) *Attorney, Agent, or Firm* — Banner & Witcoff, Ltd.

(57) ABSTRACT

Disclosed herein is a multiple light emitter device which inactivates microorganisms. The device includes at least two light emitters and at least one light-converting material arranged to convert at least a portion of light from the light emitters. Any unconverted light emitted from the light emitters and converted light emitted from the at least one light-converting material mixes to form a combined light, the combined light being white. In one aspect, the light emitters include at least one blue light emitter and at least one violet light emitter. In another aspect, the light emitters include one blue light emitter and one emitter within the range of approximately yellow to infra-red light.

26 Claims, 5 Drawing Sheets

(51) Int. Cl.
*H01L 33/50* (2010.01)
*A61L 9/18* (2006.01)
*A61L 2/08* (2006.01)
*A61N 5/06* (2006.01)

(52) U.S. Cl.
CPC .... *A61N 2005/0662* (2013.01); *H01L 33/504* (2013.01); *H01L 2933/0083* (2013.01)

(56) References Cited

U.S. PATENT DOCUMENTS

| | | | |
|---|---|---|---|
| 2,773,715 | A | 12/1956 | Lindner |
| 3,314,746 | A | 4/1967 | Millar |
| 3,670,193 | A | 6/1972 | Thorington et al. |
| 3,791,864 | A | 2/1974 | Steingroever |
| 3,926,556 | A | 12/1975 | Boucher |
| 3,992,646 | A | 11/1976 | Corth |
| 4,121,107 | A | 10/1978 | Bachmann |
| 4,461,977 | A | 7/1984 | Pierpoint et al. |
| 4,576,436 | A | 3/1986 | Daniel |
| 4,867,052 | A | 9/1989 | Cipelletti |
| 4,892,712 | A | 1/1990 | Robertson et al. |
| 4,910,942 | A | 3/1990 | Dunn et al. |
| 5,231,472 | A | 7/1993 | Marcus et al. |
| 5,489,827 | A | 2/1996 | Xia |
| 5,530,322 | A | 6/1996 | Ference et al. |
| 5,559,681 | A | 9/1996 | Duarte |
| 5,668,446 | A | 9/1997 | Baker |
| 5,721,471 | A | 2/1998 | Begemann et al. |
| 5,725,148 | A | 3/1998 | Hartman |
| 5,800,479 | A | 9/1998 | Thiberg |
| 5,901,564 | A | 5/1999 | Comeau, II |
| 5,962,989 | A | 10/1999 | Baker |
| 6,031,958 | A | 2/2000 | McGaffigan |
| 6,166,496 | A | 12/2000 | Lys et al. |
| 6,183,500 | B1 | 2/2001 | Kohler |
| 6,242,752 | B1 | 6/2001 | Soma et al. |
| 6,246,169 | B1 | 6/2001 | Pruvot |
| 6,251,127 | B1 | 6/2001 | Biel |
| 6,379,022 | B1 | 4/2002 | Amerson et al. |
| 6,477,853 | B1 | 11/2002 | Khorram |
| 6,524,529 | B1 | 2/2003 | Horton, III |
| 6,551,346 | B2 | 4/2003 | Crossley |
| 6,554,439 | B1 | 4/2003 | Teicher et al. |
| 6,627,730 | B1 | 9/2003 | Burnie |
| 6,676,655 | B2 | 1/2004 | McDaniel |
| 6,791,259 | B1 | 9/2004 | Stokes et al. |
| 6,902,807 | B1 | 6/2005 | Argoitia et al. |
| 7,015,636 | B2 | 3/2006 | Bolta |
| 7,175,807 | B1 | 2/2007 | Jones |
| 7,190,126 | B1 | 3/2007 | Paton |
| 7,198,634 | B2 | 4/2007 | Harth et al. |
| 7,201,767 | B2 | 4/2007 | Bhullar |
| 7,213,941 | B2 | 5/2007 | Sloan et al. |
| 7,438,719 | B2 | 10/2008 | Chung et al. |
| 7,476,885 | B2 | 1/2009 | Garcia et al. |
| 7,503,675 | B2 | 3/2009 | Demarest et al. |
| 7,516,572 | B2 | 4/2009 | Yang et al. |
| 7,521,875 | B2 | 4/2009 | Maxik |
| 7,611,156 | B2 | 11/2009 | Dunser |
| 7,612,492 | B2 | 11/2009 | Lestician |
| 7,658,891 | B1 | 2/2010 | Barnes |
| 7,955,695 | B2 | 6/2011 | Argoitia |
| 8,035,320 | B2 | 10/2011 | Sibert |
| 8,214,084 | B2 | 7/2012 | Ivey et al. |
| 8,232,745 | B2 | 7/2012 | Chemel et al. |
| 8,357,914 | B1 | 1/2013 | Caldwell |
| 8,398,264 | B2 | 3/2013 | Anderson et al. |
| 8,476,844 | B2 | 7/2013 | Hancock et al. |
| 8,481,970 | B2 | 7/2013 | Cooper et al. |
| 8,506,612 | B2 | 8/2013 | Ashdown |
| 8,508,204 | B2 | 8/2013 | Deurenberg et al. |
| 8,761,565 | B1 | 6/2014 | Coleman et al. |
| 8,886,361 | B1 | 11/2014 | Harmon et al. |
| 8,895,940 | B2 | 11/2014 | Moskowitz et al. |
| 8,999,237 | B2 | 4/2015 | Tumanov |
| 9,024,276 | B2 | 5/2015 | Pugh et al. |
| 9,027,479 | B2 | 5/2015 | Raksha et al. |
| 9,028,084 | B2 | 5/2015 | Maeng et al. |
| 9,039,966 | B2 | 5/2015 | Anderson et al. |
| 9,046,227 | B2 | 6/2015 | David et al. |
| 9,078,306 | B2 | 7/2015 | Mans et al. |
| 9,119,240 | B2 | 8/2015 | Nagazoe |
| 9,173,276 | B2 | 10/2015 | Van Der Veen et al. |
| 9,257,059 | B2 | 2/2016 | Raksha et al. |
| 9,283,292 | B2 | 3/2016 | Kretschmann |
| 9,313,860 | B2 | 4/2016 | Wingren |
| 9,323,894 | B2 | 4/2016 | Kiani |
| 9,333,274 | B2 | 5/2016 | Peterson et al. |
| 9,368,695 | B2 | 6/2016 | David et al. |
| 9,410,664 | B2 | 8/2016 | Krames et al. |
| 9,420,671 | B1 | 8/2016 | Sugimoto et al. |
| 9,433,051 | B2 | 8/2016 | Snijder et al. |
| 9,439,271 | B2 | 9/2016 | Ku et al. |
| 9,439,989 | B2 | 9/2016 | Lalicki et al. |
| 9,492,576 | B1 | 11/2016 | Cudak et al. |
| 9,581,310 | B2 | 2/2017 | Wu et al. |
| 9,623,138 | B2 | 4/2017 | Pagan et al. |
| 9,625,137 | B2 | 4/2017 | Li et al. |
| 9,681,510 | B2 | 6/2017 | van de Ven |
| 2002/0074559 | A1 | 6/2002 | Dowling et al. |
| 2002/0122743 | A1 | 9/2002 | Huang |
| 2003/0009158 | A1 | 1/2003 | Perricone |
| 2003/0019222 | A1 | 1/2003 | Takahashi et al. |
| 2003/0023284 | A1 | 1/2003 | Gartstein et al. |
| 2003/0124023 | A1 | 7/2003 | Burgess et al. |
| 2003/0178632 | A1 | 9/2003 | Hahn et al. |
| 2003/0207644 | A1 | 11/2003 | Green et al. |
| 2003/0231485 | A1 | 12/2003 | Chien |
| 2004/0008523 | A1 | 1/2004 | Butler |
| 2004/0010299 | A1 | 1/2004 | Tolkoff et al. |
| 2004/0024431 | A1 | 2/2004 | Carlet |
| 2004/0039242 | A1 | 2/2004 | Tolkoff et al. |
| 2004/0047142 | A1 | 3/2004 | Goslee |
| 2004/0147984 | A1 | 7/2004 | Altshuler et al. |
| 2004/0147986 | A1 | 7/2004 | Baumgardner et al. |
| 2004/0158541 | A1 | 8/2004 | Notarianni et al. |
| 2004/0159039 | A1 | 8/2004 | Yates et al. |
| 2004/0162596 | A1 | 8/2004 | Altshuler et al. |
| 2004/0230259 | A1 | 11/2004 | Di Matteo |
| 2004/0262595 | A1 | 12/2004 | Mears et al. |
| 2004/0266546 | A1 | 12/2004 | Huang |
| 2005/0055070 | A1 | 3/2005 | Jones et al. |
| 2005/0104059 | A1 | 5/2005 | Friedman et al. |
| 2005/0107849 | A1 | 5/2005 | Altshuler et al. |
| 2005/0107853 | A1 | 5/2005 | Krespi et al. |
| 2005/0159795 | A1 | 7/2005 | Savage et al. |
| 2005/0207159 | A1 | 9/2005 | Maxik |
| 2005/0212397 | A1 | 9/2005 | Murazaki et al. |
| 2005/0267233 | A1 | 12/2005 | Joshi |
| 2006/0006678 | A1 | 1/2006 | Herron |
| 2006/0009822 | A1 | 1/2006 | Savage et al. |
| 2006/0022582 | A1 | 2/2006 | Radkov |
| 2006/0071589 | A1 | 4/2006 | Radkov |
| 2006/0085052 | A1 | 4/2006 | Feuerstein et al. |
| 2006/0138435 | A1 | 6/2006 | Tarsa et al. |
| 2006/0186377 | A1 | 8/2006 | Takahashi et al. |
| 2006/0230576 | A1 | 10/2006 | Meine |
| 2006/0247741 | A1 | 11/2006 | Hsu et al. |
| 2006/0262545 | A1 | 11/2006 | Piepgras et al. |
| 2007/0023710 | A1 | 2/2007 | Tom et al. |
| 2007/0061050 | A1 | 3/2007 | Hoffknecht |
| 2007/0115665 | A1 | 5/2007 | Mueller et al. |
| 2007/0164232 | A1 | 7/2007 | Rolleri et al. |
| 2007/0258851 | A1 | 11/2007 | Fogg et al. |
| 2008/0008620 | A1 | 1/2008 | Alexiadis |
| 2008/0015560 | A1 | 1/2008 | Gowda et al. |
| 2008/0091250 | A1 | 4/2008 | Powell |
| 2008/0278927 | A1 | 11/2008 | Li et al. |
| 2008/0305004 | A1 | 12/2008 | Anderson et al. |
| 2008/0307818 | A1 | 12/2008 | Min et al. |
| 2009/0018621 | A1 | 1/2009 | Vogler et al. |
| 2009/0034236 | A1 | 2/2009 | Reuben |
| 2009/0076115 | A1 | 3/2009 | Wharton et al. |

(56) References Cited

U.S. PATENT DOCUMENTS

2009/0154167 A1 6/2009 Lin
2009/0231832 A1 9/2009 Zukauskas et al.
2009/0285727 A1 11/2009 Levy
2009/0314308 A1 12/2009 Kim et al.
2010/0001648 A1 1/2010 De Clercq et al.
2010/0027259 A1 2/2010 Simon et al.
2010/0071257 A1 3/2010 Tsai
2010/0090935 A1 4/2010 Tseng et al.
2010/0102252 A1 4/2010 Harmon et al.
2010/0107991 A1 5/2010 Elrod et al.
2010/0121420 A1 5/2010 Fiset et al.
2010/0148083 A1 6/2010 Brown et al.
2010/0179469 A1 7/2010 Hammond et al.
2010/0232135 A1 9/2010 Munehiro et al.
2010/0246169 A1 9/2010 Anderson et al.
2011/0063835 A1 3/2011 Rivas et al.
2011/0084614 A1 4/2011 Eisele et al.
2011/0256019 A1 10/2011 Gruen et al.
2011/0316025 A1* 12/2011 Kuzuhara ............. H01L 33/504 257/98
2012/0014538 A1* 1/2012 Bozkurt ................. H03G 3/001 381/107
2012/0025717 A1 2/2012 Klusmann et al.
2012/0043552 A1 2/2012 David et al.
2012/0161170 A1* 6/2012 Dubuc .................. A01G 7/045 257/89
2012/0199005 A1 8/2012 Koji et al.
2012/0273340 A1 11/2012 Felix
2012/0280147 A1 11/2012 Douglas
2012/0281408 A1 11/2012 Owen et al.
2012/0315626 A1 12/2012 Nishikawa et al.
2012/0320607 A1 12/2012 Kinomoto et al.
2013/0010460 A1 1/2013 Peil et al.
2013/0045132 A1 2/2013 Tumanov
2013/0077299 A1 3/2013 Hussell et al.
2013/0200279 A1 8/2013 Chuang
2013/0298445 A1 11/2013 Aoki et al.
2013/0313516 A1 11/2013 David et al.
2013/0313546 A1 11/2013 Yu
2013/0323375 A1* 12/2013 Takahashi .............. A23B 7/015 426/248
2014/0061509 A1 3/2014 Shur et al.
2014/0209944 A1 7/2014 Kim et al.
2014/0225137 A1 8/2014 Krames et al.
2014/0254131 A1 9/2014 Osinski et al.
2014/0265868 A1 9/2014 Morrisseau
2014/0301062 A1 10/2014 David et al.
2014/0328046 A1 11/2014 Aanegola et al.
2014/0334137 A1* 11/2014 Hasenoehrl ......... H01L 25/0753 362/147
2015/0062892 A1 3/2015 Krames et al.
2015/0068292 A1 3/2015 Su et al.
2015/0086420 A1 3/2015 Trapani
2015/0129781 A1 5/2015 Kretschmann
2015/0148734 A1 5/2015 Fewkes et al.
2015/0150233 A1 6/2015 Dykstra
2015/0182646 A1 7/2015 Anderson et al.
2015/0219308 A1 8/2015 Dross et al.
2015/0233536 A1 8/2015 Krames et al.
2015/0273093 A1 10/2015 Holub et al.
2016/0000950 A1 1/2016 Won
2016/0000953 A1 1/2016 Bettles et al.
2016/0015840 A1 1/2016 Gordon
2016/0030610 A1 2/2016 Peterson et al.
2016/0091172 A1* 3/2016 Wu ......................... F21V 13/08
2016/0114067 A1 4/2016 Dobrinsky et al.
2016/0249436 A1 8/2016 Inskeep
2016/0271280 A1 9/2016 Liao et al.
2016/0271281 A1 9/2016 Clynne et al.
2016/0273717 A1 9/2016 Krames et al.
2016/0276550 A1 9/2016 David et al.
2016/0324996 A1 11/2016 Bilenko et al.
2016/0345569 A1 12/2016 Freudenberg et al.
2016/0346565 A1 12/2016 Rhodes et al.
2016/0354502 A1 12/2016 Simmons et al.
2016/0366745 A1* 12/2016 Hikmet ................... F21K 9/232
2016/0375161 A1 12/2016 Hawkins et al.
2016/0375162 A1 12/2016 Marry et al.
2016/0375163 A1 12/2016 Hawkins et al.
2017/0014538 A1* 1/2017 Rantala ............... H01L 25/0753
2017/0030555 A1 2/2017 Lalicki et al.
2017/0081874 A1 3/2017 Daniels
2017/0094960 A1 4/2017 Sasaki et al.
2017/0100494 A1 4/2017 Dobrinsky et al.
2017/0100607 A1 4/2017 Pan et al.
2017/0281812 A1 10/2017 Dobrinsky et al.
2018/0113066 A1 4/2018 Freitag et al.
2018/0117189 A1 5/2018 Yadav et al.
2018/0117190 A1 5/2018 Bailey
2018/0117193 A1 5/2018 Yadav et al.
2018/0124883 A1 5/2018 Bailey
2018/0185533 A1 7/2018 Lalicki et al.
2018/0190625 A1 7/2018 Steckel et al.
2018/0280723 A1 10/2018 Enwemeka et al.
2018/0311386 A1 11/2018 Hawkins et al.
2019/0070323 A1 3/2019 Atreya et al.
2019/0371978 A1 12/2019 Iwasa et al.

FOREIGN PATENT DOCUMENTS

CN 105304801 A 2/2016
CN 205360038 U 7/2016
CN 106937461 A 7/2017
DE 102011001097 A1 9/2012
DE 102015207999 A1 11/2016
EP 0306301 A1 3/1989
EP 1693016 A1 8/2006
EP 1887298 A1 2/2008
EP 1943880 B1 4/2013
FR 2773715 A1 7/1999
JP 2003-332620 A 11/2003
JP 2003339845 A 12/2003
JP 2004261595 A 9/2004
JP 2004275927 A 10/2004
JP 2007511279 A 5/2007
JP 2008-004948 A 1/2008
JP 2009-004351 A 1/2009
JP 2011-513996 A 4/2011
JP 2013-045896 A 3/2013
JP 2013-093311 A 5/2013
JP 2015-015106 A 1/2015
JP 2015-035373 A 2/2015
KR 20130096965 A 9/2013
KR 101526261 B1 6/2015
KR 101648216 B1 8/2016
KR 20160127469 A 11/2016
KR 101799538 B1 11/2017
TW 201604490 A 2/2016
TW M530654 U 10/2016
WO 0114012 A1 3/2001
WO 03037504 A1 5/2003
WO 03063902 A2 8/2003
WO 03084601 A2 10/2003
WO 03089063 A1 10/2003
WO 2004033028 A2 4/2004
WO 2005048811 A2 6/2005
WO 2005049138 A1 6/2005
WO 2006023100 A1 3/2006
WO 2006100303 A2 9/2006
WO 2006126482 A1 11/2006
WO 2007012875 A1 2/2007
WO 2007035907 A2 3/2007
WO 2008071206 A1 6/2008
WO 2009056838 A1 5/2009
WO 2010110652 A1 9/2010
WO 2015066099 A2 5/2015
WO 2015189112 A1 12/2015
WO 2016019029 A1 2/2016
WO 2017009534 A1 1/2017
WO 2017205578 A1 11/2017

(56) References Cited

OTHER PUBLICATIONS

Jappe, U., "Pathological mechanisms of acne with special emphasis on Propionibacterium acnes and related therapy," Acta Dermato-Venereologica, 2003, vol. 83, pp. 241-248.
Burkhart, C. N. et al., "Assesment of etiologic agents in acne pathogenesis," Skinmed, 2003, vol. 2, No. 4, pp. 222-228.
Tong, Y., et al. "Population study of atmospheric bacteria at the Fengtai district of Beijing on two representative days," Aerobiologica, 1993, vol. 9, 1 page, Abstract only provided.
Tong, Y. et al., "Solar radiation is shown to select for pigmented bacteria in the ambient outdoor atmosphere," Photochemistry and Photobiology, 1997, val. 65, No. 1, pp. 103-106.
Marshall, J. H., et al., "Pigments of *Staphylococcus au reus*, a series of triterpenoid carotenoids," J. Bacteriology, 1981, vol. 147, No. 3, pp. 900-913.
Pelz, A. et al., "Structure and biosynthesis of staphyloxanthin production of methicillin-resistant *Staphylococcus aureus,*" Biol. Pharm. Bull., 2012, val. 35, No. 1, 9 pages.
Sakai, K., et al., "Search for inhibitors of staphyloxanthin production by methicillin-resistant *Staphylococcus aureus,*" Biol. Pharm. Bull., 2012, val. 35, No. 1, pp. 48-53.
Clauditz, A. et al., "Staphyloxanthin plays a role in the fitness of *Staphylococcus aureus*and its ability to cope with oxidative stress," Infection and Immunity, 2006, vol. 74, No. 8, 7 pages.
Feng-Chyi Duh et al, "Innovative Design of an Anti-bacterial Shopping Cart Attachment", Journal of Multidisciplinary Engineering Science and Technology (JMEST), Oct. 10, 2015, vol. 2 Issue 10, http://www.jmest.org/wp-content/uploads/JMESTN42351112.pdf.
Drew Prindle, "This UV-Emitting Door Handle Neutralizes Bacteria, Helps Fight the Spread of Disease", Digital Trends, Jun. 19, 2015, https://www.digitaltrends.com/cool-tech/uv-door-handle-kills-germs/.
Jun. 29, 2018—(DE) Office Action—App 112016003453.9.
Apr. 19, 2018—U.S. Non-Final Office Action—U.S. Appl. No. 15/886,366.
Kundrapu et al. "Daily disinfection of high touch surfaces in isolation rooms to reduce contamination of healthcare workers' hands". Journal of Infection Control and Hospital Epidemiology; vol. 33, No. 10, pp. 1039-1042, published Oct. 2012.
Sofia Pitt and Andy Rothman, "Bright idea aims to minimize hospital-acquired infections", CNBC News website, published on Dec. 9, 2014 and retrieved from website: https://www.cnbc.com/2014/12/09/bright-idea-aims-to-minimize-hospital-acquired-infections.html. 6 pages.
Sarah Ward, "LED Retrofit Health ROI? See VitalVio", Poplar Network website, published on Aug. 13, 2014 and retrieved from website: https://www.poplarnetwork.com/news/led-retrofit-health-roi-see-vitalvio. 3 pages.
International Search Report and Written Opinion issued in connection with corresponding PCT application PCT/US17/68749 dated Mar. 6, 2018.
International Search Report and Written Opinion for corresponding International Application No. PCT/US17/68755 dated Apr. 16, 2018, 17 pages.
Wang, Shun-Chung, et al.; "High-Power-Factor Electronic Ballast With Intelligent Energy-Saving Control for Ultraviolet Drinking-Waler Treatment Systems"; IEEE Transactions on Industrial Electronics; vol. 55; Issue 1; Dale of Publication Jan. 4, 2008; Publisher IEEE.
Berezow Alex, How to Kill Insects With Visible Light, Real Clear Science, Jan. 11, 2015, pp. 1-4, <https://www.realclearscience.com/journal_club/2015/01/12/how_to_kill_insects_with_visible_light_109021.html>.
Hori Masatoshi et al., Lethal Effects of Short-Wavelength Visible Light on Insects, Scientific Reports, Dec. 9, 2014, pp. 1-6, Graduate School of Agricultural Science, Tohoku University, Sendai, Japan. <https://www.semanticscholar.org/paper/Lethal-effects-of-short-wavelength-visible-light-o-Hori-Shibuya/2c11cb3f70a059a051d8ed02fff0e8a967a4c4d4>.
Master Blaster, Tohoku University Team Discovers Blue Light is Effect at Killing Insects, Sora News 24, Dec. 12, 2014, pp. 1-5, Japan, <https://en.rocketnews24.com/2014/12/12/tohoku-university-team-discovers-blue-light-is-effective-at-killing-insects/>.
Jul. 19, 2018—U.S. Final Office Action—U.S. Appl. No. 15/856,971.
Oct. 1, 2018—U.S. Advisory Action—U.S. Appl. No. 15/856,971.
Jul. 17, 2018—U.S. Final Office Action—U.S. Appl. No. 15/857,128.
Oct. 1, 2018—U.S. Advisory Action—U.S. Appl. No. 15/857,128.
Sep. 21, 2018—U.S. Non-Final Office Action—U.S. Appl. No. 16/022,440.
Nov. 1, 2018 —U.S. Final Office Action—U.S. Appl. No. 15/886,366.
Nov. 15, 2018—U.S. Non-Final Office Action—U.S. Appl. No. 16/000,690.
Dec. 3, 2018—U.S. Restriction Requirement—U.S. Appl. No. 15/856,971.
Dec. 3, 2018—U.S. Non-Final Office Action—U.S. Appl. No. 15/857,128.
Dornob, "Healthy Handle: Self-Sanitizing UV Dorr Knob Kils Germs", Dornob.com, Dec. 5, 2018, pp. 1-3, https://dornob.com/healthy-handle-self-sanitizing-uv-door-knob-kills-germs/.
Kickstarter, "Orb, The World's First Germ-Killing BLue/UV Light Ball", Dec. 10, 2018, pp. 1-10,<https://www.kickstarter.com/projects/572050089078660/orbtm-the-worlds-first-germ-killing-uv-light-ball>.
Nutone, "QTNLEDB LunAura Collection 110 CFM Fan,Light,LED Nightlight, with Tinted Light Panel, Energy Star® Certified Ventilation Fans", Dec. 11, 2018, p. 1, http://www.nutone.com/products/product/a6da75af-8449-4d4d-8195-7011ce977809.
Nutone, "NuTone Bath and Ventilation Fans", Dec. 11, 2018, pp. 1-2, http://www.nutone.com/products/filter/qt-series-fanlights-25a05450-d47b-4ab8-9992-f8c2cdat7b90.
Nutone, "ULTRA PRO™ Series Single-Speed Fans and Fan/Lights", Dec. 11, 2018, p. 1, http://www.nutone.com/products/filter/ultra-pro-series-fanlights-eb590f89-dca2-40e7-af39-06e4cccb96ca.
Dec. 12, 2018—U.S. Final Office Action—U.S. Appl. No. 15/886,420.
Nov. 27, 2018—Japanese Office Action—JP 2018-525520.
Jan. 9, 2019—U.S. Notice of Allowance amd Fee(s) Due—U.S. Appl. No. 15/940,127.
Jan. 4, 2019—Taiwan Office Action—ROC (Taiwan) Pat. Appl. No. 104124977.
Feb. 11, 2019—(WO) International Search Report—App PCT/US2018/061859.
Feb. 28, 2019—(WO) International Search Report—App PCT/US2018/061843.
Feb. 28, 2019—(WO) International Search Report—App PCT/US2018/061856.
Apr. 5, 2019—U.S. Non-Final Office Action—U.S. Appl. No. 15/886,420.
Apr. 15, 2019—(CA) Examiner's Report—App 2,993,825.
May 1, 2019—U.S. Notice of Allowance—U.S. Appl. No. 15/940,127.
May 29, 2019—U.S. Non-Final Office Action—U.S. Appl. No. 16/000,426.
May 24, 2019—U.S. Final Office Action—U.S. Appl. No. 16/000,690.
Jun. 20, 2019—U.S. Final Office Action—U.S. Appl. No. 15/857,128.
Absorption and Fluorescence Spectroscopy of Tetraphenylporphyrin§ and Metallo-Tetraphenylporphyrin, article, 2005, 11 pp., Atomic, Molecular and Supramolecular Studies.
Dayer, et al., Band Assignment in Hemoglobin Porphyrin Ring Spectrum: Using Four-Orbital Model of Gouterman, article, Sep. 8, 2009, Protein & Peptide Letters, 2010, vol. 17, No. 4, Department of Biology, Faculty of Sciences, Shahid Chamran University of Ahvaz, Tehran, Iran, 7 pages.
Ayat M. Ali, Effect of MRSA Irradiation by 632, 532, and 405 nm (Red, Blue, and Green) Diode Lasers on Antibiotic Susceptibility Tests, Article, Jun. 2007, 7 pp, vol. 59, No. 2 , 2017, J Fac Med Baghdad.
Nussbaum, et al., Effects of 630-, 660-, 810-, and 905-nm Laser Irradiation, Delivering Radiant Exposure of 1-50 J/cm2 on Three Species of Bacteria in Vitro, journal, 2002, vol. 20, No. 6, 2002, Journal of Clinical LaserMedicine & Surgery, Canada, 9 pages.

(56) References Cited

OTHER PUBLICATIONS

Kim, et al., In Vitro Bactericidal Effects of 625, 525, and 425nm Wavelength (Red, Green, and Blue) Light-Emitting Diode Irradiation, article, 2013, 9 pp., vol. 31, No. 11, 2013, Department of Oral Pathology Medical Research Center for Biomineralization Disorders School of Dentistry Dental Science Research Institute, Korea, 9 pages.
Rita Giovannetti, The Use of Spectrophotometry UV-Vis for the Study of Porphyrins, article, 2012, 23 pp., InTech Europe, Croatia.
Josefsen, et al., Unique Diagnostic and Therapeutic Roles of Porphyrins and Phthalocyanines in Photodynamic Therapy, Imaging and Theranostics, article, Oct. 4, 2012, 51 pp., 2012; 2(9):916-966. doi: 10.7150/thno.4571, Ivyspring International Publisher, Department of Chemistry, The University of Hull, Kingston-Upon-Hull, HU6 7RX, U.K., 51 pages.
Jul. 8, 2019—(WO) ISR & WO—App PCT/US2019/024593.
Aug. 1, 2019—U.S. Final Office Action—U.S. Appl. No. 15/856,971.
Sep. 13, 2019—U.S. Final Office Action—U.S. Appl. No. 16/000,426.
Sep. 25, 2019—U.S. Non-Final Office Action—U.S. Appl. No. 16/000,690.
Oct. 15, 2019—U.S. Final Office Action—U.S. Appl. No. 15/886,420.
Nov. 5, 2019—(JP) Final Office Action—JP 2018-525520.
Oct. 9, 2019—(CN) Office Action—CN 201680048598.9.
Oct. 1, 2019—(KR) Office Action—App 10-2018-7005077—Eng Tran.
Apr. 15, 2019—(CA) Office Action—App 2,993,825.
Nov. 20, 2019—(CA) Examiner's Report—App 2,993,825.
Dec. 26, 2019—(TW) Office Action and Search Report—App 107143161.
Dec. 27, 2019—(TW) Office Action and Search Report—App 108111242.
Sep. 6, 2019—(TW) Office Action—App 107143162.
Sep. 20, 2019—(TW) Office Action—App 107143577.
Jan. 29, 2020—U.S. Non-Final Office Action—U.S. Appl. No. 16/000,426.
Sep. 13, 2017—U.S. Non-Final Office Action—U.S. Appl. No. 15/223,134.
Feb. 3, 2017—U.S. Non-Final Office Action—U.S. Appl. No. 15/200,284.
Jul. 21, 2015—U.S. Non-Final Office Action—U.S. Appl. No. 14/501,931.
Feb. 25, 2020—U.S. Non-Final Office Action—U.S. Appl. No. 16/577,766.
Mar. 18, 2020—(WO) ISR & WO—App PCT/US2019/068799.
Oct. 31, 2008—(WO) ISR & WO—App PCT/GB20081003679 (Univ Strathclyde).
May 4, 2010—(WO) IPRP—App PCT/GB2008/003679 (Univ Strathclyde).
Sep. 13, 2018—U.S. Non-Final Office Action—U.S. Appl. No. 15/940,127.
Dai et al., "Blue light for infectious diseases: Propionibacterium acnes, Helicobacter pylori, and beyond?," Drug Resist Update, 15(4): 223-236 {Aug. 2012).
Halstead et al., "The antibacterial activity of blue light against nosocomial wound pathogens growing planktonically and as mature biofilms," Appl. Environ, Microbial., Apr. 2016, 38 pages, retrieved from: http://aem.asm.org/.
R.S. McDonald et al., "405 nm Light Exposure of Osteoblasts and Inactivation of Bacterial Isolates From Arthroplasty Patients: Potential for New Disinfection Applications?," European Cells and Materials vol. 25, (2013), pp. 204-214.
Tomb et al., "Inactivation of Streptomyces phage C31 by 405 nm light," Bacteriophage, 4:3, Jul. 2014, retrieved from: http://dx.doi.org/10.4161/bact.32129, 7 pages.
Tsukada et al., "Bactericidal Action of Photo-Irradiated Aqueous Extracts from the Residue of Crushed Grapes from Winemaking," Biocontrol Science, vol. 21, No. 2, (2016), pp. 113-121, retrieved from: https://www.researchgate.net/publication/304628914.
International Search Report and Written Opinion issued in connection with corresponding PCT Application No. PCT/US2016/036704 dated Dec. 8, 2016, 20 pages.
LEDs Magazine, "Lumination Vio LED combines 405 nm chip with new phosphors," retrieved from the Internet on Apr. 20, 2017 at http://www.leds.magazine.com/articles/2007/06/lumination-vio-led-combines-405-nm-chip-with-new-phosphors.html, Published Jun. 14, 2007, 2 pages.
LEDs Magazine, "ANSI evaluates revisions to SSL chromaticity standard," retrieved from the Internet on Apr. 20, 2017 at: http://www .ledsmagazine.com/articles/2011/07/ansi-evaluates-revisions-to-ssl-chromaticity-standard-magazine.html, Published Jul. 18, 2011, 4 pages.
LEDs Magazine, "ANSI works to update the solid-state lighting standard for chromaticity," retrieved from the Internet on Apr. 20, 2017 at: http://www.ledsmagazine.com/articles/print/volume-12/issue-2/features/standards/ansi-works-to-update-the-ssl-chromaticity-standard.html, Published Feb. 23, 2015, 5 pages.
LEDs Magazine, "ANSI continues advancements on SSL chromaticity standard," retrieved from the Internet on Apr. 20, 2017 at http:/lwww.ledsmagazine.com/articles/print/volume-12/issue-11/features/standards/ansi-continues-advancements-on-ssl-chromaticity-standard.html, Published Dec. 8, 2015, 6 pages.
Soraa, "PAR30L," retrieved from the Internet on Apr. 20, 2017 at: http://www_soraa.com/products/22-PAR30L, 6 pages.
Soraa, "PAR30L 18.5W," retrieved from the Internet on Apr. 20, 2017 at http://wwvv.soraa.com/products, 5 pages.
Bache et al., "Clinical studies of the High-Intensity Narrow-Spectrum light Environmental Decontamination System (HINS-light EDS), for continuous disinfection in the burn unit inpatient and outpatient settings," Burns 38 (2012), pp. 69-76.
Patent Cooperation Treaty, Search Report—Written Opinion, International Application No. PCT/US16/44634, dated Oct. 20, 2016, 14 pages.
Color Phenomena, "CIE-1931 Chromaticity Diagram," last updated Aug. 22, 2013, retrieved from www.color-theory-phenomena.nl/10.02.htm on Jan. 20, 2016, 3 pages.
Patent Cooperation Treaty, Written Opinion of the International Searching Authority and International Search Report for PCT/US2015/042678 dated Nov. 2, 2015, 13 pages.
Patent Cooperation Treaty, International Preliminary Report on Patentability for PCT/GB2008/003679 dated May 4, 2010, 9 pages.
Patent Cooperation Treaty, Written Opinion of the International Searching Authority and International Search Report or PCT/GB2008/003679 dated Oct. 31, 2008, 11 pages.
U.S. Appl. No. 15/886,420, Office Action dated May 9, 2018, 9 pages.
U.S. Appl. No. 15/223,134, Third Party Submission submitted Jun. 6, 2017, 25 pages.
Yi, Notice of Allowance and Fee(s) due for U.S. Appl. No. 14/501,931 dated Jan. 20, 2016, 8 pages.
Yu, J. et al., "Efficient Visible-Light-Induced Photocatalytic Disinfection on Sulfur-Doped Nanocrystalline Titania," Environ. Sic. Technol., 39, 2005, pp. 1175-1179.
Demidova, T. et al., "Photodynamic Therapy Targeted to Pathogens," International Journal of Immunipathology and Pharmacology, 17(3), pp. 245-254.
Ashkenazi, H. et al., "Eradication of Propionibacterium acnes by its endogenic porphyrins after illumination with high intensity blue light," FEMS Immunology and Medical Microbiology, 35, pp. 17-24.
Elman, M. et al., "The Effective Treatment of Acne Vulgaris by a High-intensity, Narrow Band 405-420 nm Light Source," Cosmetic & Laser Ther, 5, pp. 111-116.
Sikora, A. et al., "Lethality of visable light for *Escherichia coli*hemH 1 mutants influence of defects in DNA repair," DNA Repair, 2, pp. 61-71.
Huffman, D. et al., "Inactivation of Bacteria, Virus and Cryptospordium by a Point-of-use Device Using Pulsed Broad Spectrum White Light," Wat. Res. 34(9), pp. 2491-2498.
Papageorgiou, P. et al., "Phototherapy with Blue (415 nm) and Red (660 nm) Light in the Treatment of Acne Vulgaris," British Journal of Dermatology, 2000, pp. 973-978.

(56) References Cited

OTHER PUBLICATIONS

Burchard, R. et al., "Action Spectrum for Carotenogenesis in Myxococcus xanthus," Journal of Bateriology, 97(3), 1969, pp. 1165-1168.
Wainwright, "Photobactetial activity of phenothiazinium dyes against methicillin-resistant strains of *Staphylococcus aureus,*" Oxford University Press Journals, retrieved from: http://dx.doi.org/10.1111/j.1574-6968.1998.tb12908.x on Jul. 23, 2015, 8 pages.
Yoshimura et al., "Antimicrobial effects of phototherapy and photochemotherapy in vivo and in vitro," British Journal of Dermatology, 1996, 135: 528-532.
Wilson et al., "Killing of methicillin-resistant *Staphylococcus aureus* by low-power laser light," J. Med, Microbial., vol. 42 (1995), pp. 62-66.
Kawada et al., "Acne Phototherapy with a high-intensity, enhanced, narrow-band, blue light source: an open study and In vitro investigation," Journal of Dermatological Science 30 (2002) pp. 129-135.
Maclean et al., "High-intensity narrow-spectrum light inactivation and wavelength sensitivity of *Staphylococcus auresu,*" FEMS Microbial. Lett., vol. 285 (2008) pp. 227-232.
Reed, "The History of Ultraviolet Germicidal Irradiation for Air Disinfection," Public Health Reports, Jan.-Feb. 2010, vol. 125, 13 pages.
Ward, "Experiments on the Action of Light on Bacillus anthracis," 10 pages.
Hamblin et al., "Helicobacter pylori Accumulates Photoactive Porphyrins and Is Killed by Visable Light," Antimicrobial Agents and Chemotherapy, Jul. 2005, pp. 2822-2827.
Dai et al., "Blue Light Rescues Mice from Potentially Fatal Pseudomonas aeruginosa Burn Infection: Efficacy, Safety, and Mechanism of Action," Antimicrobial Agents and Chemotherapy, Mar. 2013, vol. 57{3), pp. 1238-1245.
Holzman, "405-nm Light Proves Potent at Decontaminating Bacterial Pathogens," retrieved from: http://forms.asm.org/microbe/index.asp?bid=64254 on Aug. 6, 2015, 34 pages.
Guffey et al., "In Vitro Bactericidal Effects of 405-nm and 470-nm Blue Light," Photomedicine and Laser Surgery, vol. 24, No. 6, retrieved from: https:/lwww.liebertpub.com/doi/abs/10.1089/pho.2006.24.684 on Mar. 23, 2018, 2 pages, abstract only provided.
Kristoff et al., "Loss of photoreversibility for UV mutation in *E. coli* using 405 nm or near-US challenge," Mutat Res., May 1983, 109{2): 143-153, 2 pages, abstract only provided.
Turner et al., "Comparative Mutagenesis and Interaction Between Near-Ultraviolet {313- to 405-nm) and Far-Ultraviolet 254-nm) Radiation in *Escherichia coli* Strains with Differeing Repair Capabilities," Journal of Bacteriology, Aug. 1981 , pp. 410-417.
Knowles et al., "Near-Ultraviolet Mutagenesis in Superoxide Dismutase-deficient Strains of *Escherichia coli,*" Environmental Health Perspectives, vol. 102{1), Jan. 1994, pp. 88-94.
Jagger, "Photoreactivation and Photoprotection," Photochemistry and Photobiology, vol. 3, Issue 4, Dec. 1964, retrieved from: https://onlinelibrary.wiley.com/doi/abs/10.1111/0751-1097.1964.tb08166.x on Mar. 23, 2018, 4 pages, abstract only provided.
Chukuka et al., Visible 405 nm SLD light photo-destroys metchicillin-resistant *Staphylococcus aureus* {MRSA) in vitro, Lasers in Surgery and Medicine, vol. 40, Issue 10, Dec. 8, 2008, retrieved from: https://onlinelibrary.wiley.com/doi/abs/10.1002/lsm.20724 on Mar. 23, 2018, 4 pages, abstract only provided.
Bek-Thomsen, M., "Acne is Not Associated with Yet-Uncultured Bacteria," J. Clinical Microbial., 2008, 46{10), 9 pages.
Harrison, A.P., "Survival of Bacteria," Annu. Rev. Microbial, 1967, p. 143, vol. 21.
Feuerstein et al., "Phototoxic Effect of Visible Light on Porphyromonas gingivalis and Fusobacterium nudeatum: An In Vitro Study," Photochemistry and Photobiology, vol. 80, Issue 3, Apr. 30, 2007, retrieved from: https://onlinelibrary.wiley.com/doi/abs/10.1111/j.1751-1097.2004.lb00106.x on Mar. 23, 2018, abstract only.
Pochi, P.E., "Acne: Androgens and microbiology," Drug Dev, Res., 1988, val. 13, 4 pages, abstract only provided.

* cited by examiner

MULTIPLE LIGHT EMITTER FOR INACTIVATING MICROORGANISMS

CROSS-REFERENCE TO RELATED APPLICATIONS

This application is a continuation application of U.S. application Ser. No. 15/940,127, filed Mar. 29, 2018 and entitled, "Multiple Light Emitter for Inactivating Microorganisms." U.S. application Ser. No. 15/940,127 is hereby incorporated by reference in its entirety.

TECHNICAL FIELD DISCLOSURE

The present disclosure concerns a multiple light emitter device capable of emitting light that can be perceived as white or a hue of white, and more particularly, a multiple light emitter device capable of emitting light that can be perceived as white or a hue of white while simultaneously causing the inactivation of microorganisms.

BACKGROUND OF THE DISCLOSURE

Light-emitting devices are a primary requirement in most indoor occupied environments to provide illumination of the area, of tasks being completed in the area, and of the area's occupants and objects. Lighting technologies range widely for use indoors, from incandescent and halogen bulbs, to fluorescent and light-emitting diode (LED) bulbs and devices, among many other technologies. The primary purpose of these lighting technologies to date is to provide light that can be observed by humans as what is considered "white" light, which can effectively illuminate different colors, textures, and features of objects in a manner pleasing to humans.

While many technologies are commercially used in lighting, LED lighting is growing as a technology to provide efficient, high quality white light illumination at an effective cost point. Some common LEDs for general illumination use a semiconductor junction that is energized to emit blue light and that is combined with a phosphor material, such as cerium-doped yttrium aluminum garnet (YAG:Ce) to convert a portion of that blue light to other wavelengths of light, such as yellow wavelengths. When balanced properly, the combined light emitted from the semiconductor junction and the phosphor material is perceived as white or a hue of white. Blue light-emitting semiconductors are used currently for many reasons, including high efficiency, relatively low cost, and relatively desirable color benefits of the blue light contribution to the overall spectrum of light (as compared to light-emitting semiconductors that emit light of another color).

Some alternative LED technologies use semiconductor junctions that emit UV, near UV, or violet light instead of blue light. A phosphor material is combined to convert a portion of the blue, violet, or UV light to other wavelengths of light and the two components are balanced appropriately to provide white or a hue of white light. Violet LEDs are used less frequently due to typically lower efficiency and cost performance, but have commercially been shown to be able to provide an adequate visual quality of light according to some standards, like the Color Rendering Index (CRI).

With both of these LED technologies, achieving a relatively high luminous efficacy of emitted radiation is balanced against achieving desirable color characteristics (CRI, correlated color temperature (CCT), Gamut, etc.) of the emitted radiation. In other words, the spectrum of combined light emitted from the lighting device is chosen, in relation to the spectral sensitivity of the human eye, to achieve high efficiency, while minimizing the sacrifice of desired color characteristics.

Alternative light sources have been created with additional performance factors in mind that utilize emitted light in different manners. Lighting fixtures and devices for horticulture, health, warmth, and disinfection have been demonstrated. In addition to being tuned for luminous efficacy of radiation, these lighting fixtures and devices are tuned to provide increased outputs of certain regions of radiation to accomplish the additional performance factor.

These lighting fixtures and devices provide a dual or multiple function of lighting through the use of various alternative functions of light such as photochemical, photobiological, radiant energy, and others. Typically, radiant energy outputs are attempted to be optimized for specific regions matching absorption or activation spectrums of the added function. For example, light fixtures and devices for horticulture are attempted to be optimized for emitting light matching absorption or activation spectrums of chlorophyll and other plant based photo-activated mechanisms. Light fixtures and devices for assisting circadian rhythm are attempted to be optimized for emitting light matching absorption or activation spectrums of melatonin.

In these lighting fixtures and devices that emit light for multiple functions, the light emissions can be balanced to achieve an acceptable level of each function. One of the functions can be general illumination (e.g., when the multiple-function lighting fixtures and devices are used in spaces occupied by humans), in which case, achieving a relatively high luminous efficacy of the emitted light is balanced not only against achieving desirable color characteristics of the emitted light, but also of achieving the one or more other functions to an acceptable or desired level.

Another function for devices that emit light for multiple functions can be disinfection (inactivation of microorganisms), in which case, the use of violet disinfecting light (e.g., 380 nm to 420 nm) is desired. As noted above, current methods of producing white light with an LED very often use a blue light (e.g., 440 nm to 495 nm) emitting semiconductor die as the base emitter and the blue light is then converted to a white light spectrum after at least a portion of the blue light passes through a wavelength conversion layer. Simply adding violet light to this existing white light spectrum does not create a visually appealing or acceptable white light for indoor illumination, instead a light with an undesirable violet hue would be created. The correct balance of colors is required to create a desirable white light that includes violet disinfecting light.

BRIEF DESCRIPTION OF THE DISCLOSURE

Embodiments of the disclosure provided herein may include a light emitting device for inactivating microorganisms, the light emitting device including at least two light emitters, wherein at least one of the at least two light emitters is configured to emit light having a wavelength in the range of 380 nm to 420 nm, at least one of the at least two light emitters is configured to emit light having a wavelength in the range of 440 nm to 495 nm, one or more of the at least two light emitters includes a light-converting material arranged to be in a direct path of the light emitted from a given light emitter with the exception that at least one light emitter configured to emit light having a wavelength in the range of 380 nm to 420 nm does not include a light-converting material, each light-converting material being arranged to convert the wavelength of the light emitted from the given light emitter to a wavelength different therefrom, and the light from any light emitter not passing through a light-converting material combines with the light emitted from each light-converting material to form white light.

Embodiments of the disclosure provided herein may include a light emitting device for inactivating microorganisms, the light emitting device including at least two light emitters, wherein at least one of the at least two light emitters is configured to emit light having a wavelength in the range of 380 nm to 420 nm, at least one of the at least two light emitters is configured to emit light having a wavelength in the range of 440 nm to 495 nm, each of the at least two light emitters includes a light-converting material arranged to be in a direct path of the light emitted from a given light emitter, each light-converting material being arranged to convert the wavelength of the light emitted from the given light emitter to a wavelength different therefrom, and the light from any light emitter not passing through a light-converting material combines with the light emitted from each light-converting material to form white light.

Embodiments of the disclosure provided herein may include a light emitting device for inactivating microorganisms, the light emitting device comprising: at least two light emitters, wherein: at least one first light emitter is configured to emit light having a wavelength in the range of 560 to 1400 nanometers (nm), the at least one first light emitter including an upconverting nanoparticle layer in a direct path of the light emitted therefrom and arranged to convert the wavelength of the light emitted to a wavelength in a range of 380-420 nm; and at least one second light emitter is configured to emit light having a wavelength in the range of 440 nm to 495 nm, the at least one second light emitter including at least one light-converting material arranged to be in a direct path of the light emitted therefrom, each light-converting material being arranged to convert the wavelength of the light emitted from the at least one second light emitter to a wavelength different therefrom, wherein the light from the at least one first and second light emitters combines to form white light.

BRIEF DESCRIPTION OF THE DRAWINGS

These and other features of the disclosure will be more readily understood from the following detailed description of the various aspects of the disclosure taken in conjunction with the accompanying drawings that depict various aspects of the disclosure.

Figure 1:
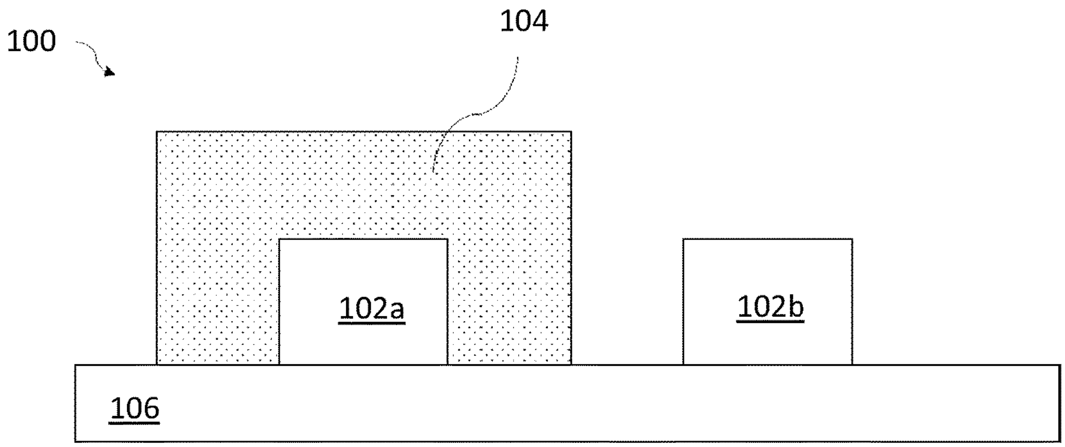
FIG. 1 illustrates a light-emitting device having a combination of blue and violet light emitters wherein at least one violet light emitter remains uncovered by a light-converting material.

It is noted that the drawings may not be to scale. The drawings are intended to depict only typical aspects of the disclosure, and therefore should not be considered as limiting the scope of the disclosure. In the drawings, like numbering represents like elements between the drawings. The detailed description explains embodiments of the disclosure, together with advantages and features, by way of example with reference to the drawings.

DETAILED DESCRIPTION OF THE DISCLOSURE

According to various embodiments, a multiple light emitter device is disclosed that is capable of emitting light that can be perceived as white or a hue of white and simultaneously is capable of emitting certain concentrations of light with specific wavelengths that are associated with the inactivation of at least some microorganisms. The various embodiments of the disclosure provide an alternative and more efficient way of producing a disinfecting white light spectrum that can be defined as white light by ANSI standards.

In embodiments of the disclosure, the light emitting device is composed of at least two light emitters (e.g., LEDs, OLEDs, semiconductor dies, lasers) and one or more light-converting materials (e.g., phosphors, optical brighteners, quantum dots, phosphorescent materials, fluorophores, fluorescent dyes, conductive polymers) assembled in a manner that light emitted from a light emitter can be directed into the light-converting material(s) and at least a portion of this light directed into the light-converting material(s) can be converted by the light-converting material(s) to light having a different quality (e.g., a different peak wavelength). Light can be converted by the light-converting material(s) by absorbing the light, which energizes or activates the light-converting material(s) to emit light of a different quality (e.g., a different peak wavelength).

Figure 2:
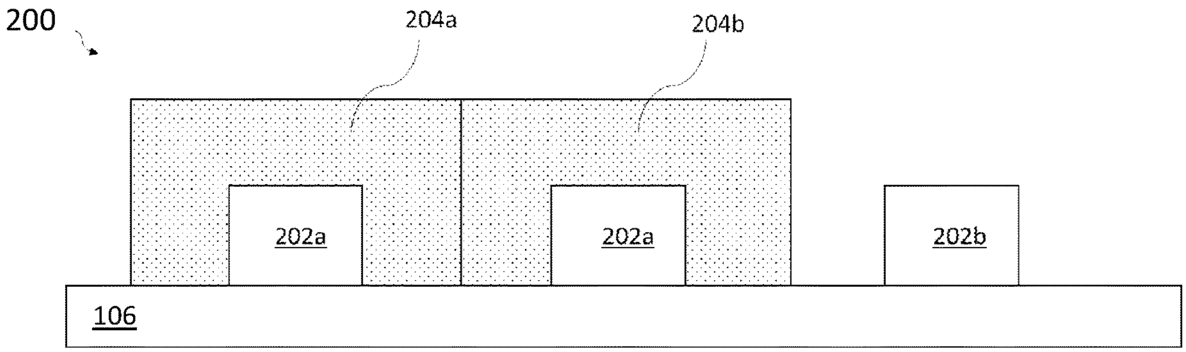
FIG. 2 illustrates another light-emitting device having a combination of blue and violet light emitters wherein at least one violet light emitter remains uncovered by a light-converting material and all emitters having a light-converting material arranged thereover are blue light emitters.
Figure 3:
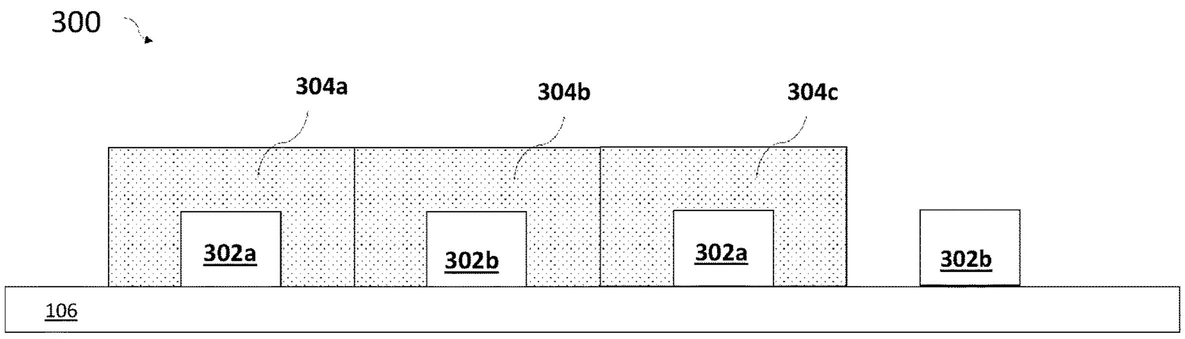
FIG. 3 illustrates another light-emitting device having a combination of blue and violet light emitters wherein at least one violet light emitter remains uncovered by a light-converting material and the emitters having a light-converting material arranged thereover are a combination of blue and violet light emitters.
Figure 4:
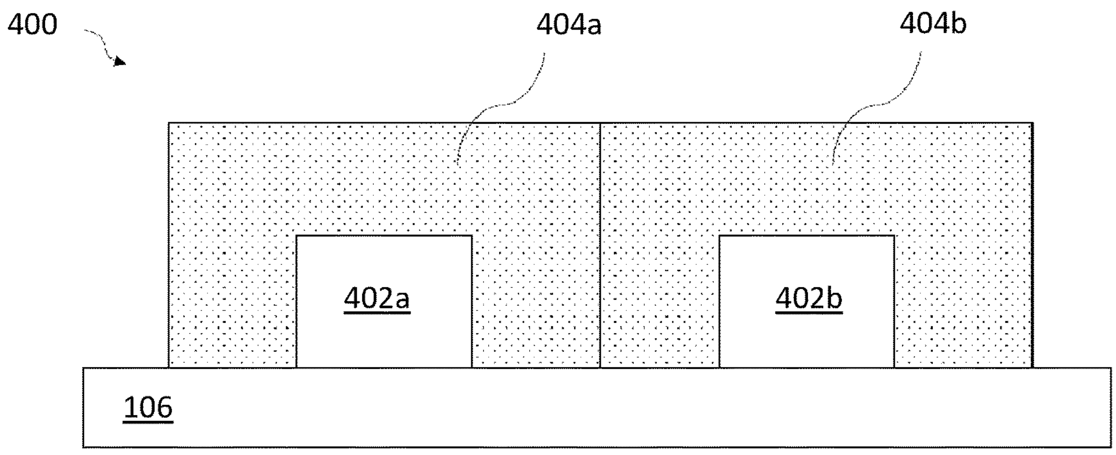
FIG. 4 illustrates another light-emitting device having a combination of blue and violet light emitters wherein all of the emitters have a light-converting material arranged thereover.
Figure 7:
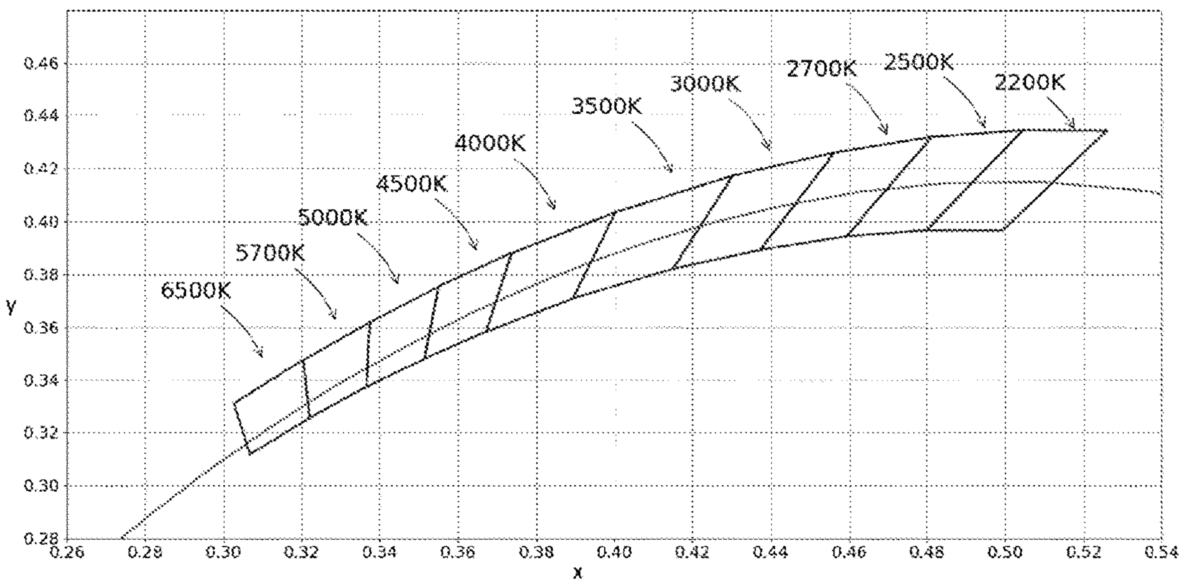
FIG. 7 illustrates an American National Standards Institute (ANSI) C78.377-2017 White Light Standards diagram using the International Commission on Illumination (CIE) 1931 x,y coordinate system with accepted x-y coordinates at selected CCTs that are color coordinate ranges for light-emitting devices in some embodiments of the disclosure.
Figure 8:
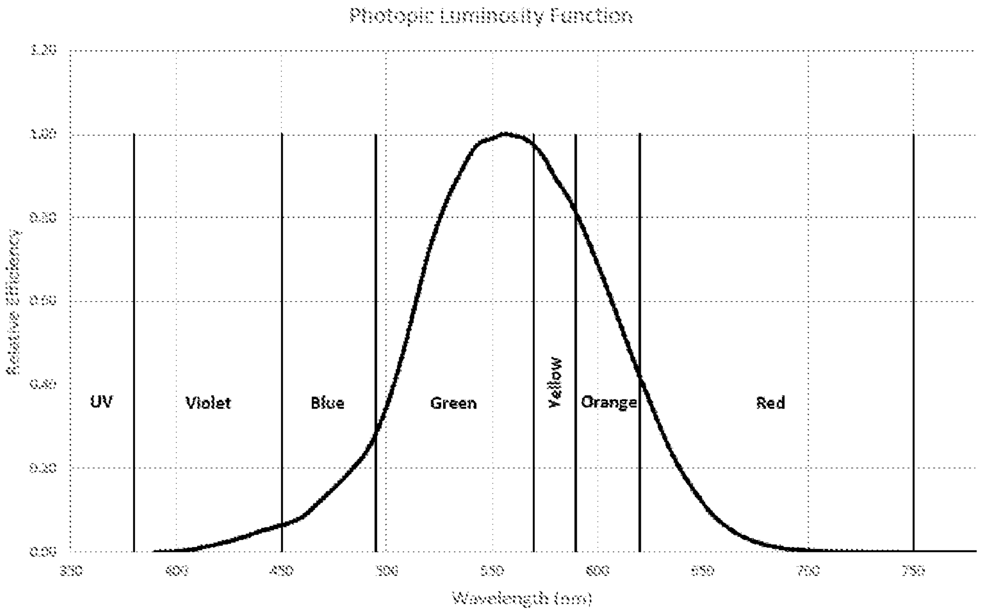
FIG. 8 illustrates a photopic luminosity function graph (eye color sensitivity graph) showing desired relative efficiency versus wavelength of light for light-emitting devices in some embodiments of the disclosure.

The light emitters and light-converting material(s) may be assembled in many different manners, such as, but not limited to embodiments of a first aspect of the disclosure depicted in FIGS. 1-3, an embodiment of a second aspect of the disclosure depicted in FIG. 4, and embodiments of a third aspect of the disclosure also depicted in FIG. 4. The light emitting devices of the disclosure can be modified by optics (e.g., a lens), reflectors, or other assembly components or materials (e.g., an encapsulant), as depicted in FIGS. 7-8, which can facilitate the combined light emitted by the light emitting device being perceived as white or a hue of white.

In a first aspect of the disclosure, the light emitting device includes at least two light emitters, for instance, at least two semiconductor dies, wherein at least one semiconductor die emits violet light within the range of 380-420 nanometers and is not covered by a light-converting material, allowing this violet wavelength to be emitted untouched, while at least one other semiconductor die emits blue light within the range of 440-495 nanometers and is covered by at least one light-converting material. The blue light passing through the light converting material creates an off-white exiting light, this exiting light combines with the violet light emitted from the uncovered semiconductor die to create a high quality disinfecting white light. The off-white exiting light is carefully designed using select light-converting material combinations to ensure that when mixed with a specific proportion of violet light, high quality white light is created. The off-white light coordinates should be above the blackbody curve on the International Commission on Illumination (CIE) 1931 Chromaticity diagram (see FIG. 9 discussed below) in order to combine with the violet light, whose coordinates are below the blackbody curve on the CIE 1931 Chromaticity diagram, to form a white light that falls on the blackbody curve or within the ANSI Quadrangles (e.g., defined by ANSI C78.377-2017) which define coordinate ranges for white light at varying color temperatures. In other words, the off-white exiting light coordinates should be above a boundary line defined as:

$$y=-2.57862x^2+2.58744x-0.209201$$

on the CIE 1931 Chromaticity diagram. In addition, the off-white light combines with the light emitted from the at least one light emitter not including the light-converting material and within the range of 380 nm to 420 nm. The light emitted in the 380-420 nm range is defined on the CIE 1931 Chromaticity diagram with coordinates below a boundary line defined as:

$$y=-2.57862x^2+2.58744x-0.209201.$$

As noted, the white light is defined on the CIE 1931 Chromaticity diagram with coordinates within one of the quadrangles defined by ANSI C78.377-2017, see FIG. 7.

In an embodiment of the first aspect of the disclosure, FIG. 1 illustrates a light emitting device 100 that includes two light emitters 102*a* and 102*b*, a light-converting material 104 and a substrate 106. One of light emitters 102 emits blue light having a wavelength in the range of 440 nm to 495 nm, i.e., light emitter 102*a*, and one of light emitters 102 emits violet light having a wavelength in the range of 380 nm to 420 nm, i.e., light emitter 102*b*. While only two light emitters 102 are shown in FIG. 1, there may be three, four, five, etc., light emitters 102 present in light-emitting device 100 so long as at least one violet light emitter 102*b* (that which emits light having a wavelength in the range of 380 nm to 420 nm) remains uncovered by light-converting material 104 (see, e.g., FIG. 2 for three light emitters and FIG. 3 for four light emitters).

Light emitter, as used herein, can be any known emitter, including but not limited to a light emitting diode (LED), an organic LED (OLED), a laser, and a semiconductor die. A single LED can include one or more semiconductor dies that are each emitters within an LED package. Blue light emitters can have a peak wavelength/majority of light output in the 440-495 nm wavelength range of light. Violet light emitters can have a peak wavelength/majority of light output in the 380-420 nm wavelength range.

Light-converting material, as used herein, constitutes a broad category of materials, substances, or structures that have the capability of absorbing a certain wavelength of light and re-emitting it as another wavelength of light. Light-converting materials should be noted to be different from light-emitting materials and light-transmitting/filtering materials. Light-emitting materials can be broadly classified as materials, substances, or structures/devices that convert a non ultraviolet-visible-infrared (UV-VIS-IR) form of energy into a UV-VIS-IR light emission. Non ultraviolet-visible-infrared (UV-VIS-IR) forms of energy may be, and are not limited to: electricity, chemical reactions/potentials, microwaves, electron beams, and radioactive decay. Light-converting materials may be contained in or deposited on a medium, making a light-converting medium. It should be understood that light-converting materials, light-converting mediums, light-converting filters, phosphors, and any other terms regarding the conversion of light are meant to be examples of the light-converting material disclosed.

In some embodiments, the light-converting material can be a phosphor, an optical brightener, a combination of phosphors, a combination of optical brighteners, or a combination of phosphor(s) and optical brightener(s). In some embodiments, the light-converting material can be quantum dots, a phosphorescent material, a fluorophore, a fluorescent dye, a conductive polymer, or a combination of any one or more types of light-converting materials.

Some example phosphors include those that convert light to each of red (620-750 nm), green (495-570 nm), and blue (440-495 nm) wavelengths, such as Nitride, Lutetium Aluminum Garnet, and $Ca_2PO_4Cl:Eu^{2+}$, respectively. Other possible phosphor material compositions include aluminate phosphors (e.g., calcium aluminate, strontium aluminate, yttrium aluminate), silicate phosphors, garnet phosphors, nitride phosphors, oxynitride phosphors, Calcium Sulfide, $Ca_2PO_4Cl:Eu^{2+}$, LSN ($La_3Si_6N_{11}:Ce^{3+}$), LYSN ($(La,Y)_3Si_6N_{11}:Ce^{3+}$), CASN ($CaAlSiN_3:Eu^{2+}$), SCASN ($(Sr,Ca)AlSiN_3:Eu^{2+}$), KSF ($K_2SiF_6:Mn^{4\pm}$), CSO ($CaSc_2O_4:Ce^{3+}$), β-SiAlON ($(Si,Al)_3(O,N)_4:Eu^{2+}$), Yttrium Aluminum Garnet (YAG: $Y_3(Al,Ga)_5O_{12}:Ce^{3+}$), Lutetium Aluminum Garnet (LuAG: $Lu_3Al_5O_{12}:Ce^{3+}$) and SBCA ($(Sr,Ba)_{10}(PO_4)_6C_{12}:Eu^{2+}$).

Optical brighteners are light-converting materials (e.g., chemical compounds) that absorb light in the ultraviolet and/or violet regions of the electromagnetic spectrum, and re-emit light in the blue region. Some optical brightening agents are chemical derivatives of stilbene, coumarin, 1, 3 diphenyl pyrazoline, naphthalene dicarboxylic acid, heterocyclic dicarboxylic acid, and cinnamic acid.

Light converting materials for use specifically with OLEDs include, for example, phosphorescent materials, fluorophores, fluorescent dyes, conductive polymers, and organometallic phosphors.

Quantum dots are nanometer sized semiconductor particles that can emit light of one or more specific wavelengths when electricity or light is applied to them. The light emitted by quantum dots can be precisely tuned by changing the size, shape and/or material of the quantum dots. Quantum dots that convert light to shorter (i.e., higher energy) wavelengths are sometimes referred to as upconverting nanoparticles (UCNPs). Quantum dots can have varying composition and structures that allow them to be classified into different types such as core-type quantum dots, core-shell quantum dots, and alloyed quantum dots. Core-type quantum dots are single component materials with uniform internal compositions, for example, chalcogenides (selenides, sulfides or tellurides) of metals like cadmium, lead or zinc (e.g., CdTe or PbS). The photo- and electroluminescence properties of core-type quantum dots can be fine-tuned by changing the crystallite size. Core shell quantum dots have small regions of a first material (core) surrounded by a second material having a wider band gap than the first material (shell) and typically offer improved quantum yield; for example, a CdSe core surrounded by a ZnS shell exhibits greater than 50% quantum yield. Alloyed quantum dots include both homogeneous and gradient internal structures and allow for tuning of both optical and electronic properties by changing the composition and internal structure without changing the crystallite size; for example, alloyed quantum dots of the composition $CdS_xSe_{1-x}/ZnS$ (with 6 nm diameter) can emit light of different wavelengths by adjusting the composition. Light-converting materials can be capable of absorbing multiple different wavelengths of light and emitting multiple different wavelengths of light, in both scaled and not specifically scaled manners.

The phosphor or other light converting material may be deposited directly on the light emitter, as illustrated in at least FIGS. 1-6, or may be remote or further removed from the light emitter. Light-converting materials can be deposited, for example, as conformal coatings, doped encapsulants or binder materials, and remote phosphors. The at least one light-converting material may be fully homogenized at different or identical ratios and used as a bulk mix, or the at least one light-converting materials may have some or all portions positioned or layered separately, affecting the absorption and emission of different materials that may not be compatible when mixed or that may absorb too much underlying light.

Substrate 106 may include but is not limited to: sapphire, silicon carbon (SiC), gallium nitride (GaN), or silicon (Si). An LED package substrate (not shown), which would be under substrate 106, may include, for example, a metal reflector cup and then an epoxy molding compound (EMC) or polycyclohexylene-dimethylene terephthalates (PCT) package. Light emitters, as described herein, may include any now known or later developed material appropriate for the stated wavelength such as but not limited to indium gallium nitride (InGaN) or gallium nitride (GaN), for violet light.

In another embodiment of the first aspect of the disclosure, FIG. 2 illustrates a light emitting device 200 that includes three light emitters 202, light-converting materials 204*a* and 204*b*, and substrate 106. The embodiment of FIG. 2 differs from FIG. 1 in that multiple blue light emitters 202*a* are covered by light-converting material 204, each of the multiple blue light emitters 202*a* emitting light having a same wavelength in the range of 440 nm to 495 nm, whereas the violet light emitter 202*b* that remains uncovered by a light-converting material emits violet light having a different wavelength, i.e., a wavelength in the range of 380 nm to 420 nm. While only three light emitters 202 are shown in FIG. 2, there may be four, five, six etc. light emitters 202 present in light-emitting device 200 so long as at least one violet light emitter 202*b* (that which emits light having a wavelength in the range of 380 nm to 420 nm) remains uncovered by light-converting material 204. As also illustrated in FIG. 2, while blue light emitters 202*a* are the same, each light emitter 202*a* has a unique light-converting material 204 thereover, for instance light-converting material 204*a* over a first blue light emitter 202*a* and light-converting material 204*b* over a second blue light emitter 202*a*, and so on.

In yet another embodiment of the first aspect of the disclosure, FIG. 3 illustrates a light-emitting device 300 that includes four light emitters 302, light-converting materials 304*a*, 304*b* and 304*c*, and substrate 106. The embodiment of FIG. 3 differs from FIG. 2 in that the multiple light emitters 302 covered by light-converting material 304 include a mixture of blue and violet light emitters 302, said mixture including a least one blue light emitter 302*a* emitting light having a wavelength in the range of 440 nm to 495 nm and at least one violet light emitter 302*b* emitting light having a wavelength in the range of 380 nm to 420 nm. Similar to that of FIG. 2, at least one violet light emitter 302*b* of the embodiment of FIG. 3 remains uncovered by a light-converting material and emits violet light having a wavelength in the range of 380 nm to 420 nm. While four light emitters 302 are shown in FIG. 3, there may be three, five, six, seven etc. light emitters 302 present in light-emitting device 300 so long as at least one violet light emitter 302*b* (that which emits light having a wavelength in the range of 380 nm to 420 nm) remains uncovered by light-converting material 304.

In a second aspect of the disclosure, the light emitting device comprises at least two light emitters, for instance, at least two semiconductor dies, wherein at least one semiconductor die emits violet light within the range of 380-420 nanometers, and at least one other semiconductor die emits blue light within the range of 440-495 nanometers, each semiconductor die being covered by at least one light-converting material. The light exiting the light-converting material(s) is carefully designed using select light-converting material combinations to ensure that when mixed, high quality white light is created.

In an embodiment of the second aspect of the disclosure, FIG. 4 illustrates a light-emitting device 400 that includes two light emitters 402, light-converting materials 404*a* and 404*b*, and substrate 106. The embodiment of FIG. 4 differs from that of FIG. 1, for example, in that all of light emitters 402 present in light-emitting device 400 include a light-converting material 404 thereover. As also illustrated in FIG. 4, each light emitter 402 has a unique light-converting material 404 thereover, for instance light-converting material 404*a* over a first light emitter 402*a* and light-converting material 404*b* over a second light emitter 402*b*, and so on. It is noted that in the embodiment of FIG. 4, at least one of light emitters 402 emits blue light having a wavelength in the range of 440 nm to 495 nm, i.e., light emitter 402*a*, and at least one of light emitters 402 emits violet light having a wavelength in the range of 380 nm to 420 nm, i.e., light emitter 402*b*. While only two light emitters 402 are shown in FIG. 4, there may be three, four, five, etc. light emitters 402 present in light-emitting device 400 so long as all light emitters 402 have a light-converting material 404 thereover.

In a third aspect of the disclosure, the light emitting device comprises at least two light emitters, wherein: at least one first light emitter is configured to emit light having a wavelength in the range of 560 to 1400 nanometers (nm), the at least one first light emitter including an upconverting nanoparticle layer (e.g., quantum dots, upconverting nanoparticles (UCNPs) as may be appropriate) in a direct path of the light emitted therefrom and arranged to convert the wavelength of the light emitted to a wavelength in a range of 380-420 nm; and at least one second light emitter is configured to emit light having a wavelength in the range of 440 nm to 495 nm, the at least one second light emitter including at least one light-converting material arranged to be in a direct path of the light emitted therefrom, each light-converting material being arranged to convert the wavelength of the light emitted from the at least one second light emitter to a wavelength different therefrom, wherein the light from the at least one first and second light emitters combines to form white light.

In an embodiment of the third aspect of the disclosure, FIG. 4 illustrates a light-emitting device 400 that includes two light emitters 402*a*, 402*b*. At least one first light emitter

404*a* is configured to emit light having a wavelength in the range of 560 to 1400 nanometers (nm). First light emitter(s) 404*a* including an upconverting nanoparticle layer 404*a* (e.g., quantum dots or other type of upconverting nanoparticles (UCNPs) as may be appropriate) in a direct path of the light emitted therefrom and arranged to convert the wavelength of the light emitted to a wavelength in a range of 380-420 nm. At least one second light emitter 402*b* is configured to emit light having a wavelength in the range of 440 nm to 495 nm. Second light emitter(s) 402*b* include at least one light-converting material 404*b* arranged to be in a direct path of the light emitted therefrom. Each light-converting material 404*b* is arranged to convert the wavelength of the light emitted from the at least one second light emitter 402*b* to a wavelength different therefrom. The light from the at least one first and second light emitters 402*a*, 402*b* combine to form white light. While only two light emitters 402*a*, 402*b* are shown in FIG. 4, there may be three, four, five, etc., light emitters of each type present in light-emitting device 400. Any number of light emitters 402*a* present in light-emitting device 400 may include UCNP layer 404*a*, and any number of second light emitters 402*b* present in light emitting device 400 may include a light-converting material 404*b* thereover.

Figure 5:
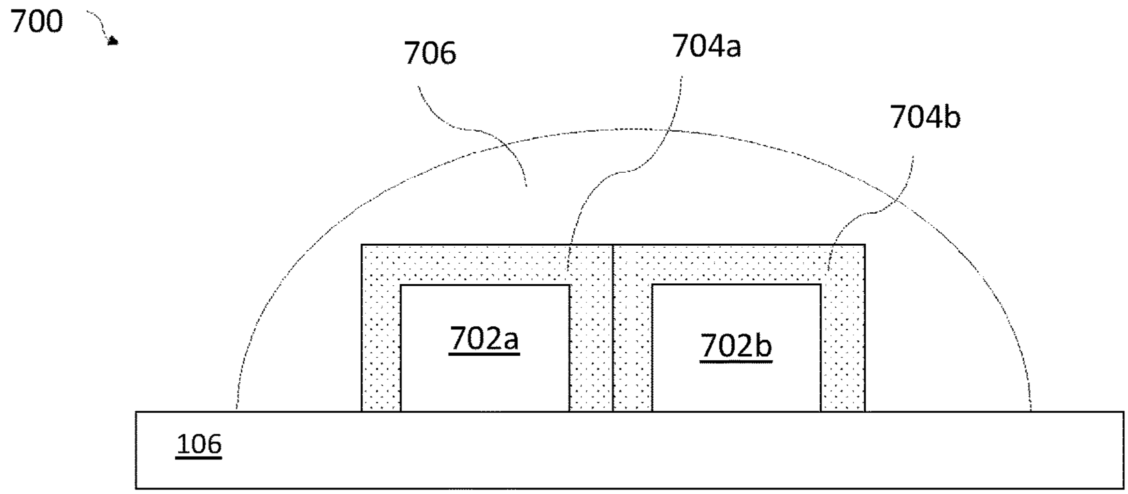
FIG. 5 illustrates another light-emitting device, similar to that of FIG. 1 but with a lens containing the emitters and light-converting material.
Figure 6:
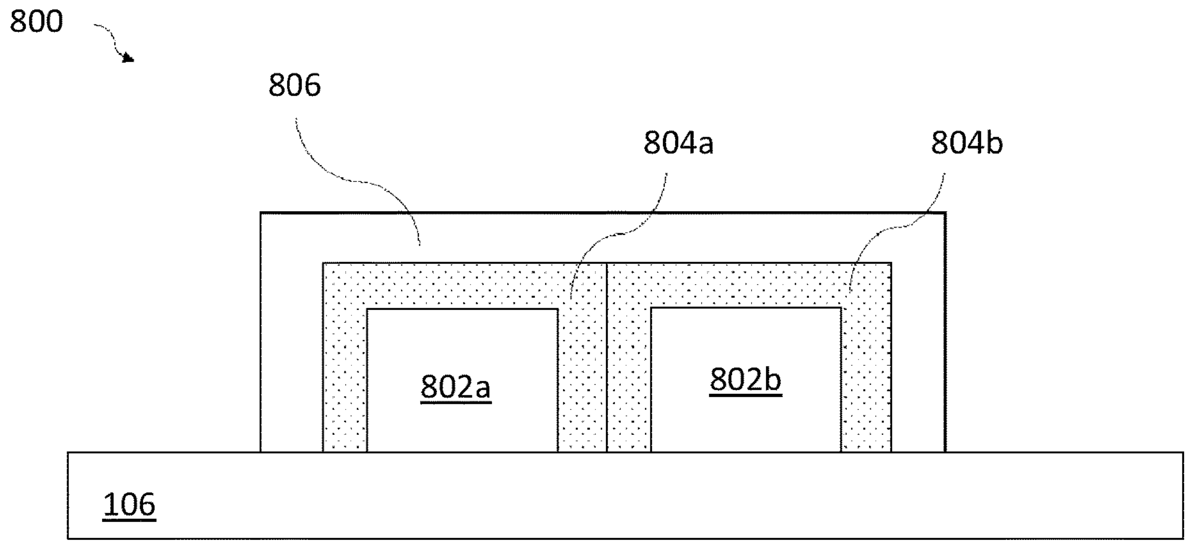
FIG. 6 illustrates another light-emitting device, similar to that of FIG. 5 but with an encapsulant containing the emitters and light-converting material.

As mentioned above, the light emitting devices of the disclosure can be modified by components such as a lens, an encapsulant, etc. FIG. 5 illustrates a light-emitting device 700 like that of FIG. 4 (for exemplary purposes only) with the addition of a lens 706 containing light-converting materials 704*a* and 704*b* and light emitters 702*a* and 702*b*. FIG. 6 illustrates a light-emitting device 800 like that of FIG. 4 (for exemplary purposes only) with the addition of an encapsulant 806 containing light-converting materials 804*a* and 804*b* and light emitters 802*a* and 802*b*.

As also mentioned above, FIG. 7 is a graphical depiction of ANSI C78.377-2017 white light standards with accepted x-y coordinates at selected CCTs. This standard, as depicted in graphical form, includes 7-step MacAdam ellipses, and shows quadrangles at various color temperatures for light-emitting devices in some embodiments of the disclosure. The ANSI C78.377-2017 standard states: "The purposes of this standard are, first, to specify the range of chromaticities recommended for general lighting with solid-state lighting products to ensure high-quality white light and, second, to categorize chromaticities with given tolerances so that the white light chromaticity of the products can be communicated to consumers." Thus, the noted ANSI standard tries to define a chromaticity range (defined as "4-step" or "7-step" Quadrangles in the CIE 1931 x,y diagram, or the CIE 1976 u',v' diagram) for high quality white lights at different CCT values. The quadrangles set color consistency bounds so that LED to LED, or even fixture to fixture, lights look consistent. The 4-step or 7-step Quadrangles also help establish how far away from a particular CCT a light can be and still be considered that particular nominal CCT. The device disclosed enables a disinfecting white light that can fall within the bounds of the Quadrangles at various color temperatures through the precise combination of selected emitters and light converting materials as described in embodiments of this disclosure. More specifically, the combined white light emitted from a light emitting device of the present disclosure can be quantified using (x,y) coordinates falling on the CIE 1931 Chromaticity diagram. The color temperature of the combined white light can vary between 1000K to 8000K for different embodiments. The (x,y) coordinates can be determined from a measured Spectral Power Distribution (SPD) graph of the emitted white light spectrum. When graphed, these determined (x,y) coordinates will fall within the bounds of a quadrangle for the color temperature of each embodiment, and thus the combined light emitted can be defined as white light using the ANSI C78.377-2017 standard.

FIG. 7 serves as an example of color coordinates and ranges of color coordinates that could be achieved in practice in some embodiments of the disclosure. It should be understood that this is an example of some existing standards of color coordinates that can be achieved; other standards that exist or may be developed in the future for white light may be used. Additionally, the disclosed device may be approximately matched in color coordinates to CIE standard illuminants and/or standard illuminant families; it should be noted that the disclosed device may not match all defined characteristics of a standard illuminant, but in some embodiments will approximately match the xy color coordinates. Some of these additional CIE standard illuminants include but are not limited to A, B, C, D50, D55, D65, D75, E, F1, F2, F3, F4, F5, F6, F7, F8, F9, F10, F11, and F12.

In some embodiments of the disclosure, a combined light emitted by the light emitters and the light-converting material(s) is white and has one or more of the following properties: (a) a proportion of spectral energy (also sometimes referred to as spectral content) measured in an approximately 380 nm to approximately 420 nm wavelength range of greater than approximately 10%, (b) a proportion of spectral energy measured in an approximately 380 nm to approximately 420 nm wavelength range of less than approximately 50%, (c) a correlated color temperature (CCT) value of 1000K to 8000K, (d) a color rendering index (CRI) value of 55 to 100, (e) a color fidelity (Re) value of 60 to 100, and (f) a color gamut ($R_g$) value of 60 to 140. Further, in some embodiments, the white light has a proportion of spectral energy measured in a 440 nm to 495 nm wavelength range of no less than 6%.

In embodiments of the disclosure, the light-emitting device can have a spectral energy of light output in the 380-420 nm wavelength range of at least 10% and/or less than approximately 50%. The spectral energy of light output in the 380-420 nm wavelength range is defined as the proportion of irradiance value of light having wavelengths in the range of 380-420 nm relative to the irradiance value of light having wavelengths in the range of 380-720 nm. Dividing the former value by the latter value yields the % spectral energy of emitted light in the 380-420 nm wavelength range. The spectral output is defined as the radiometric energy. In some embodiments, the irradiance values are measured in milliWatts ($mW/cm^2$) of radiometric energy. The irradiance values can be measured by any now-known or later-developed means. In one example, irradiance values can be that at a target surface, e.g., a floor, desktop, lab bench top, door knob, etc., and can be any necessary level to inactivate microorganisms, e.g., at least 0.01 $mW/cm^2$, measured from 380-420 nm. Alternatively, each LED package may have some minimum amount of radiometric energy, perhaps 20 mW measured from 380-420 nm. In another example, a goal may be set to have a minimum intensity, e.g., of 500 lux, on target surfaces of white light. Here, as long as violet content is above 20%, one can assume disinfection at that white light intensity. In other words, as long as violet content is known, a time period for effective disinfection can be calculated. In some embodiments, the light-emitting device can have a spectral energy of light output in the 380-420 nm wavelength range of at least approximately 20%, 25%, 30%, 35%, 40%, 45%, or 50%. In some embodiments, the light-emitting device can have a spectral energy of light output in the 380-420 nm wavelength range of less than approximately 50%, 45%, 40%, 35%, or 30%. Further, in some embodiments, the white light has a proportion of spectral energy (calculated as described above relative to 380-420 nm) measured in a 440 nm to 495 nm wavelength range no less than 6%.

The spectral energy in the 380-420 nm wavelength range can be utilized for the inactivation of bacterial pathogens. A 405 nm peak wavelength and a range of wavelengths above and below 405 nm (380-420 nm) have proven effective for the inactivation of bacterial pathogens. Light in the 380-420 nm wavelength is capable of killing or deactivating microorganisms such as but not limited to Gram positive bacteria, Gram negative bacteria, bacterial endospores, mold and yeast and filamentous fungi. Some Gram positive bacteria that can be killed or deactivated include *Staphylococcus aureus* (incl. MRSA), *Clostridium perfringens, Clostridium difficile, Enterococcus faecalis, Staphylococcus epidermidis, Staphyloccocus hyicus, Streptococcus pyogenes, Listeria monocytogenes, Bacillus cereus, Mycobacterium terrae, Lactococcus lactis, Lactobacillus plantarum, Bacillus circulans* and *Streptococcus thermophilus*. Some Gram negative bacteria include *Acinetobacter baumannii, Pseudomonas aeruginosa, Klebsiella pneumoniae, Proteus vulgaris, Escherichia coli, Salmonella enteritidis, Shigella sonnei, Serratia* spp. and *Salmonella typhimurium*. Some bacterial endospores include *Bacillus cereus* and *Clostridium difficile*. Some yeast and filamentous fungi include *Aspergillus niger, Candida albicans*, and *Saccharomyces cerevisiae*. Light in the 380-420 nm wavelength has been effective against every type of bacteria tested, although it takes different amounts of time or dosages dependent on species. Based on known results it is expected to be effective against all gram-negative and gram-positive bacteria to some extent over a period of time. It can also be effective against many varieties of fungi, although these will take longer to show an effect.

To kill or deactivate microorganisms on a target surface, a certain intensity of light from a lighting device/fixture is typically required. In some embodiments of the disclosure, a light emitting device emitting light with an irradiance of at least 0.01 mW/cm$^2$ (in the 380-420 nm range) on the target surface is attained.

In embodiments of the disclosure, white light can be defined as light with a correlated color temperature (CCT) value of approximately 1000 Kelvin (K) to approximately 8000K, in some embodiments approximately 2000K to approximately 6000K, and in some embodiments approximately 2,500K to approximately 5,000K, wherein "approximately" can include plus or minus about 200K.

In some embodiments, the CRI value of the combined light output or combined emitted light from the light-emitting device (e.g., light emitted from the light emitters mixed with light emitted from the light-conversion material(s)) can have a CRI value of at least 55, 60, 65, 70 or 75. In further embodiments, the CRI value can be at least 80, 85, 90, or 95, plus or minus approximately 5 (allowing for a CRI value of 100).

White light can also be defined according to a variety of other industry standards such as but not limited to: the ANSI C78.377-2017 White Light Standard, described above with respect to FIG. 7, the Fidelity Index ($R_f$) which provides a color fidelity value, and the Gamut Index ($R_g$) which provides a color gamut value. Sometimes $R_f$ and $R_g$ values are reported in combination as the "TM-30-15" Standard. $R_f$ represents how closely the color appearances of an entire sample set are reproduced (rendered) on average by a test light as compared to those under a reference illuminant. Thus, $R_f$ combines the computed color differences for all test-color samples in one single average index value, and is only one aspect of color quality not considering perception/preference effects. $R_g$ provides information about the relative range of colors that can be produced (via reflection) by a white light source. A score close to 100 indicates that, on average, the light source reproduces colors with similar levels of saturation as an incandescent bulb (2700K) or daylight (5600K/6500K).

In some embodiments, the light-emitting device can be a surface mount LED device, which includes an LED and at least one light-conversion material. The surface mount LED device can be mounted onto a printed circuit board ("PCB") or otherwise configured to be capable of transferring power to the light-emitting device and to the LED. The LED can be coupled to the PCB through bond wires or leads which enable an electrical connection from the LED to the outside of the device. The device may have a lens, encapsulant, or other protective cover (see, e.g., FIGS. 5-6). The embodiments shown in FIGS. 1-6 can be embodied as surface mount LED devices by arranging them with wires or leads connected to the respective LEDs and configured to be connected to a PCB.

In additional embodiments, the light-emitting device can be a through-hole LED device, which is similar to a surface mount package but is intended to be mounted to a PCB board or otherwise configured to be capable of transferring power into the device and the light emitter via conductive legs which mate with matched holes or vias on the PCB or similar structure. The legs are coupled to the PCB or similar structure through solder or another conductive medium.

In some embodiments, the light-emitting device can be a chip-on-board LED arrangement, which is a package with multiple light emitters and a light converting-material. The multiple light emitter can be mounted directly to a substrate, and the light-converting material can be placed so a desired portion of emitted light is converted by the light converting material.

In another embodiment, the light-emitting device can be a chip scale package (CSP) or a flip chip CSP, both of which packages the emitters without using a traditional ceramic/plastic package and/or bond wires, allowing the substrate to be attached directly to the printed circuit board.

Unlike typical multiple light emitter devices which require the emitted light to be combined/mixed in an optical chamber (by way of, e.g., optics or housing structures) which in turn requires increased electronics, controls, optics, and housing structures, and ultimately results in increased cost, embodiments of the disclosure do not require multiple light emissions to be combined through optics or housing structures. Multiple light emitter devices of the disclosure are configured such that the emitted light is combined/mixed before it exits a given LED package and thus does not require combining/mixing in the optical chamber.

Multiple dies used within a single LED package to create a disinfecting white light spectrum like those of the disclosure is a significant improvement over previous fixture level, multiple LED, color mixing methods. A typical color mixing method entails using multiple LEDs in separate packages of varying colors, at least one of which emits disinfecting violet light, which requires a secondary optic within the light fixture to allow the colors to mix together to form white light. Complicated electrical controls are often required to correctly balance the output of each individual LED to form white light. Previous fixture designs are also complicated and expensive since they require the integration of secondary optics to mix the colors. Such complicated controls and increased amount of required LEDs, limits the applications available to this color mixing method to mainly larger overhead lighting products, whereas single white disinfecting LEDs can be easily integrated into products of varying shapes and sizes.

Furthermore, in embodiments of the disclosure, using a blue light emitter to create a major portion of the white light spectrum is also significantly more efficient than using a violet light emitter to create the entire spectrum because the blue wavelength does not need to be converted as far within the visible spectrum range (e.g., 380-750 nm) with the wavelength converting materials to the additional colors that mix together to form the white light. Because blue light has a longer wavelength than violet light, it is more efficient to convert to even longer wavelengths because of reduced Stoke's loss. There is a higher Stoke's shift using violet light which reduces conversion efficiency as compared to using blue light. In addition to more efficient light conversion, blue semiconductor dies are more readily available on the market than violet dies for mass manufacturing of LEDs. Moreover, most phosphors that have been developed and are available on the market are optimized for use with a blue emitting semiconductor die, making access to phosphors easier. LEDs compete on the market based on efficiency, which is improved with the light emitting devices of the disclosure. Sufficient blue light also helps a white light spectrum achieve a higher CRI which can improve a human's perception of the white light. Since some people barely see violet light while others see violet light somewhat brightly, adding blue light to the white light spectrum also helps add to the consistency of the light perceived from person to person.

Humans perceive different colors of light at different brightness's within the visible spectrum. The brightness perceived by humans converts to an output in Lumens, which contributes to the Lumens/Watt efficiency. A high efficiency is ideal, which outputs more Lumens at a given power. Green (e.g., approximately 555 nanometers) is seen brightest by humans, this is evidenced by the eye color sensitivity graph of FIG. 8. The closer the wavelength is to green on the spectrum, the more it contributes to Lumen output. Violet light (e.g., 380-420 nanometers) contributes very little to Lumen output as seen on the graph as well. Blue light (e.g., 440-495 nanometers) is much closer to green and contributes significantly more to Lumen output than violet light. Including a blue phosphor converted die and a violet die within one LED package, such as in embodiments of the disclosure described above, is more efficient for this reason. The off-white exiting light has a much higher lumen output on its own, with the bonus of also including the disinfecting energy from the violet die which contributes to harmful microorganism inactivation. The addition of the violet die to a blue phosphor converted die is much more efficient than using only a violet die.

The foregoing description of various aspects of the disclosure has been presented for the purpose of illustration and description. It is not intended to be exhaustive or to limit the disclosure to the precise form disclosed, and obviously, many modifications and variations are possible. Such variations and modifications that may be apparent to one skilled in the art are intended to be included within the scope of the present disclosure as defined by the accompanying claims.

What is claimed:

1. A light emitting device for inactivating microorganisms, the light emitting device comprising:

at least two light emitters, wherein:

a first light emitter of the at least two light emitters is configured to emit a first light for inactivating microorganisms comprising a wavelength in a range of 380 nanometers (nm) to 420 nm, wherein no light converting material is arranged in a direct path of the first light;

a second light emitter of the at least two light emitters is configured to emit a second light comprising a wavelength in a range of 440 nm to 495 nm; and a light-converting material arranged in a direct path of the second light and configured to convert a portion of the second light to a third light having a wavelength different therefrom, wherein the first light combines with the second light and the third light to form white disinfecting light.

2. The light emitting device of claim 1, wherein the light-converting material comprises one or more of a phosphor, an optical brightener, a quantum dot, a phosphorescent material, a fluorophore, a fluorescent dye, or a conductive polymer.

3. The light emitting device of claim 1, wherein the white disinfecting light has a correlated color temperature (CCT) value within a range of 1000 Kelvin (K) to 8000 K.

4. The light emitting device of claim 1, wherein the white disinfecting light has a color rendering index (CRI) value within a range of 55 to 100.

5. The light emitting device of claim 1, wherein the white disinfecting light has a proportion, greater than 10%, of spectral energy measured in a 380 nm to 420 nm wavelength range.

6. The light emitting device of claim 1, wherein the white disinfecting light has a proportion, less than 50%, of spectral energy measured in a 380 nm to 420 nm wavelength range.

7. The light emitting device of claim 1, wherein the white disinfecting light has a proportion of spectral energy measured in a 440 nm to 495 nm wavelength range of no less than 6%.

8. The light emitting device of claim 1, wherein microorganisms are inactivated upon illumination with the white disinfecting light emitted by the light emitting device.

9. The light emitting device of claim 1, wherein one or more of the first light emitter or the second light emitter comprise a light-emitting diode (LED), an organic light-emitting diode (OLED), a semiconductor die, or a laser.

10. The light emitting device of claim 1, wherein the second light combines with the third light to form an off-white light defined on International Commission on Illumination (CIE) 1931 Chromaticity diagram with coordinates above a boundary line defined as:

$$y=-2.57862x^2+2.58744x-0.209201.$$

11. The light emitting device of claim 1, wherein the first light is defined on International Commission on Illumination (CIE) 1931 Chromaticity diagram with coordinates below a boundary line defined as:

$$y=-2.57862x^2+2.58744x-0.209201.$$

12. The light emitting device of claim 1, wherein the white disinfecting light is defined on International Commission on Illumination (CIE) 1931 Chromaticity diagram with coordinates within a quadrangle defined by American National Standards Institute (ANSI) C78.377-2017.

13. The light emitting device of claim 1, wherein the first light comprises a radiometric energy of at least 20 milliwatts (mW).

14. A method for inactivating microorganisms, the method comprising:

emitting, via a first light emitter, a first light for inactivating microorganisms comprising a first wavelength in a range of 380 nanometers (nm) to 420 nm, wherein no light converting material is arranged in a direct path of the first light;

emitting, via a second light emitter, a second light comprising a second wavelength in a range of 440 nm to 495 nm;

causing conversion, via a light-converting material arranged in a direct path of the second light emitter, of a first portion of the second light to a third light comprising a third wavelength different from the first wavelength; and forming, based on the first light, the second light, and the third light, white disinfecting light.

15. The method of claim 14, wherein the light-converting material comprises one or more of a phosphor, an optical brightener, a quantum dot, a phosphorescent material, a fluorophore, a fluorescent dye, or a conductive polymer.

16. The method of claim 14, wherein forming the white disinfecting light comprising forming the white disinfecting light with a correlated color temperature (CCT) value within a range of 1000 Kelvin (K) to 8000 K.

17. The method of claim 14, wherein forming the white disinfecting light comprising forming the white disinfecting light with a color rendering index (CRI) value within a range of 55 to 100.

18. The method of claim 14, wherein forming the white disinfecting light comprises forming a white disinfecting light with a proportion, greater than 10%, of spectral energy measured in a 380 nm to 420 nm wavelength range.

19. The method of claim 14, wherein forming the white disinfecting light comprises forming a white disinfecting light with a proportion, less than 50%, of spectral energy measured in a 380 nm to 420 nm wavelength range.

20. The method of claim 14, wherein forming the white disinfecting light comprises forming a white disinfecting light with a proportion, at least 6%, of spectral energy measured in a 440 nm to 495 nm wavelength range.

21. The method of claim 14, further comprising:

initializing, based on illumination via the white disinfecting light, inactivation of microorganisms.

22. The method of claim 14, wherein one or more of the first light emitter or the second light emitter comprise a light-emitting diode (LED), an organic light-emitting diode (OLED), a semiconductor die, or a laser.

23. The method of claim 14, further comprising:

forming, based on the second light and the third light, off-white light defined according to International Commission on Illumination (CIE) 1931 Chromaticity diagram with coordinates above a boundary line defined as:

$$y=-2.57862x2+2.58744x-0.209201.$$

24. The method of claim 14 wherein the first light is defined according to International Commission on Illumination (CIE) 1931 Chromaticity diagram with coordinates below a boundary line defined as:

$$y=-2.57862x2+2.58744x-0.209201.$$

25. The method of claim 14, wherein forming the white disinfecting light comprises forming a white disinfecting light defined on International Commission on Illumination (CIE) 1931 Chromaticity diagram with coordinates within a quadrangle defined by American National Standards Institute (ANSI) C78.377-2017.

26. The method of claim 14, wherein the first light comprises a radiometric energy of at least 20 milliwatts (mW).

* * * * *